United States Patent [19]

Roizman et al.

[11] Patent Number: 4,769,331

[45] Date of Patent: Sep. 6, 1988

[54] RECOMBINANT METHODS AND MATERIALS

[75] Inventors: Bernard Roizman, Chicago, Ill.; Leonard E. Post, Kalamazoo, Mich.

[73] Assignee: University Patents, Inc., Westport, Conn.

[21] Appl. No.: 690,369

[22] Filed: Jan. 9, 1985

Related U.S. Application Data

[63] Continuation of Ser. No. 302,497, Sep. 16, 1981, abandoned.

[51] Int. Cl.$^4$ .................. C12N 15/00; C12N 9/00; C12N 9/12; C12N 7/00; C12N 7/04; C12P 21/00; C12P 19/34
[52] U.S. Cl. .................. 435/172.3; 435/68; 435/91; 435/172.1; 435/183; 435/194; 435/235; 435/236; 435/320; 935/23; 935/32; 935/57
[58] Field of Search .......... 435/172.3, 317, 68, 435/70, 71, 91, 240, 241, 235, 236, 172.1, 320, 194, 240.1, 240.2; 935/23, 32, 57

[56] References Cited

U.S. PATENT DOCUMENTS 4,237,224  12/1980  Boyer ...................... 435/68

FOREIGN PATENT DOCUMENTS 0022685  1/1981  European Pat. Off. ........... 435/172
81/02426  9/1981  PCT Int'l Appl. ............... 435/68

OTHER PUBLICATIONS

Mocarski et al.; Cell, 22, 243, (1980).
Post et al.; Cell, 24, 555, 25, 227, (1981).
Scherer et al.; Proc. Natl. Acad. Sci., U.S.A., 76, 4951, (1979).
Scherer et al.; Science, 209, 1380, (1980).
Struhl et al.; Proc. Natl. Acad. Sci., U.S.A., 76, 1035, (1979).
Enquist et al.; Gene, 7, 335, (1979).
Kit et al.; Cytogenet. Cell Genetl., 26, 93, (1980).
Szostak et al.; Plasmid, 2, 536, (1979).
Honess, et al., J. Virol., 14, pp. 8–19, (1974).
Honess, et al., Proc. National Acad. Sci. U.S.A., 72, pp. 1276–1280, (1975).
Morse, et al., J. Virol., 26, pp. 389–410, (1978).
Preston, et al., J. Virol., 28, pp. 499–517, (1978).
Clements, et al., Nucleic Acids Res., 7, pp. 77–91, (1979).
Anderson, et al., J. Virol., 34, pp. 9≧27, (1980).
Perucho, et al., Nature, 285, pp. 207–210, (1980).
Pellicer, et al., Science, 209, pp. 1414–1422, (1980).
Lowy, et al., Cell, 22, pp. 817–823, (1980).
Mackem, et al., Proc. National Acad. Sci. U.S.A., 77, pp. 7122–7126, (1980).

*Primary Examiner*—James Martinell
*Attorney, Agent, or Firm*—Barbara A. Shimei

[57] ABSTRACT

Specific DNA sequence insertions, deletions and substitutions (i.e., combinations of sequence deletion and insertion) in eukaryotic cell or viral genomes are stably effected through use of selectable DNA sequences comprising a herpesvirus thymidine kinase (tk) gene.

9 Claims, 6 Drawing Sheets

RECOMBINANT METHODS AND MATERIALS

The invention described herein was made in the course of work partly supported by a grant from the National Institutes of Health.

This application is a continuation, of application Ser. No. 302,497, filed Sept. 16, 1981, now abandoned.

BACKGROUND

The present invention relates generally to genetic engineering of eukaryotic cellular or viral genomes at specific sites.

A focus of genetic engineering in the recent past has been the use of recombinant DNA methodologies for the purification and amplification of genetic material. U.S. Pat. No. 4,237,224 to Cohen, et al., for example, relates to transformation of procaryotic unicellular host organisms with "hybrid" viral or circular plasmid DNA which includes exogenous DNA sequences. The procedures of the Cohen, et al. patent first involve manufacture of a transformation vector by enzymatically cleaving viral or circular plasmid DNA to form linear DNA strands. Selected foreign DNA strands are also prepared in linear form through use of similar enzymes. The linear viral or plasmid DNA is incubated with the foreign DNA in the presence of ligating enzymes capable of effecting a restoration process, and "hybrids" are formed which include the selected foreign DNA segment "spliced" into the viral or circular DNA plasmid. Transformation of compatible unicellular host organisms with the hybrid vector results in the formation of multiple copies of the foreign DNA in the host cell population. In some instances, the desired result is simply the amplification of the foreign DNA and the "product" harvested is DNA. More frequently, the goal of transformation is the expression by the host cells of the foreign DNA in the form of large scale synthesis of isolatable quantities of commercially significant protein or polypeptide fragments coded for by the foreign DNA.

The success of procedures such as described by Cohen, et al. is due in large part to the ready availability of restriction endonuclease enzymes which facilitate the site-specific cleavage of both the unhybridized DNA vector and, e.g., eukaryotic DNA strands containing the foreign sequences of interest. Cleavage in a manner providing for the formation of complimentary "ends" on the linear DNA strands greatly enhances the likelihood of functional incorporation of the foreign DNA into the vector upon ligating enzyme treatment. Verification of hybrid formation is facilitated by chromatographic techniques which can, for example, distinguish the hybrid plasmids from non-hybrids on the basis of molecular weight. Other useful verification techniques involve radioactive DNA hybridization.

Another manipulative "tool" largely responsible for successes in transformation of procaryotic cells is the use of selectable "marker" gene sequences. Briefly put, hybrid vectors are employed which contain, in addition to the desired foreign DNA, one or more DNA sequences which code for expression of a phenotypic trait capable of distinguishing transformed from non-transformed host cells. Typical marker gene sequences are those which allow a transformed procaryotic cell to survive and propagate in a culture medium containing metals, antibiotics, and like components which would kill or severely inhibit propagation of nontransformed host cells.

In vivo recombination of homologous DNA sequences has been a powerful tool in systems where selections exist for the recombination event. Standard techniques of bacterial genetics rely on recombination of exogenous DNA with homologous DNA on the bacterial chromosome. See, e.g. Miller, *Experiments In Molecular Genetics,* Coldspring Harbor Laboratory (1972). Recent studies involving introduction of DNA into yeast cells have also shown that recombination of the introduced DNA occurs at homologous sites in the yeast genome. See, e.g., Szostak, et al., *Plasmid,* 2, pp. 536–554 (1979) and Scherer, et al., *Science,* 209, 1380–1384 (1980).

Another major focus of genetic engineering has been the manipulation of eukaryotic cell and viral genomes for purposes of attempting correction of genetic defects and modifying antigenicity and pathogenicity of viruses. Such manipulations are significantly more difficult than those involved in the above-noted Cohen, et al. host/vector methodology owing to the larger size and greater complexity of the genomes involved. While a typical DNA plasmid (e.g., *Escherichia coli* plasmid pBR322) contains about 5,000 nucleotides, the genomes of pathogenic viruses such as herpes virus, pseudorabies and bovine rhinotracheitis virus contain upwards of 150,000 nucleotides. Eukaryotic cell genomes are larger still, involve diploid associations, and are very likely to include multiple alleles of genes of interest.

Site-specific restriction endonuclease enzymes which so greatly facilitate manipulations on small plasmids and bacterial phage DNA are often useless for manipulative work on larger genomes owing to the proliferation of "target" cleavage sites therein. Cleavage of large genomes can be accomplished with relative ease but the existence of multiple cleavage sites renders virtually impossible the properly sequenced reassembly of the genome with ligating enzymes. Thus, while large genomes can readily be fragmented and "mapped" using restriction endonucleases, the enzymatic tools necessary for single, site-specific insertions and deletions are simply not available.

In a like manner, marker gene sequences commonly employed in verification of transformation of procaryotic cell lines are of little use in monitoring for specific insertions and deletions in more complex eukaryotic cell and viral genomes. To be effective in the verification of insertions and/or deletions in such large genomes, marker genes must be susceptible to use in very powerful selection procedures for both the presence and absence of the gene in a transformant genome. They should also be readily obtained and amplified, and should preferably have a relatively small size for convenience in manipulation.

Thus, despite the extensive need for manipulation of eukaryotic cell and viral genomes at specific sites and despite the relative ease of identifying specific DNA sequences which might advantageously be inserted into or deleted from such genomes, the art is without access to procedures which will permit such manipulations and the formation of specifically engineered genomes.

Pertinent to the background of the invention is the disclosure of Pellicer, et al., *Science,* 209, pp. 1414–1422 (1980) that DNA obtained from viruses and eukaryotic cells has been used to transfer genes coding for growth transformation enzyme, thymidine kinase (tk), adenine phosphoribosyltransferase (APRT) and hypoxanthine-guanine phosphoribosyltransferase (HGPRT) to mutant eukaryotic cell populations deficient for such functions. [See also, Perucho, et al., *Nature*, 285, pp. 207–210 (1980) for discussion of transfers involving cellular thymidine kinase (i.e., chicken tk) and Lowy, et al., *Cell*, 22, pp. 817–823 (1980) for discussion of hamster APRT gene characteristics.]

Although Pellicer, et al. report transformation of thymidine kinase deficient (tk−) mouse fibroblast cells to at least transitorily incorporate herpesvirus tk genes derived from Herpes Simplex Type 1 virus (HSV-l), such transformations have been non-specific as to the site of gene insertion. Due in part to the non-specific nature of insertion, none of the genetic transformations has been or could be purposefully "reversed" by deletion of the inserted tk gene and corresponding reversion of the genome to its initial tk− state.

The disclosures of applicants and their co-workers appearing in Mocarski, et al., *Cell*, 22, pp. 243–245 (November, 1980), Post, et al., *Cell*, 24, pp. 555–565 (May, 1981) and Post, et al., *Cell*, 25, pp. 227–232 (July, 1981) provide information pertinent to the background of the invention.

BRIEF SUMMARY

The present invention provides novel, highly efficient methods for effecting insertion, deletion and substitution (i.e., combinations of sequence deletion and insertion) of selected DNA sequences at specific sites in eukaryotic cell and viral genomes.

Methods of the present invention involve use of a readily available, conveniently manipulated herpesvirus thymidine kinase gene as a marker gene sequence in procedures which allow the easy monitoring of transformational events on the basis of selection for and against the presence of the viral tk gene in the subject genome. Viral tk genes employed in the procedures are preferably of human Herpes Simplex (HSV-1 and HSV-2) origin.

Products of the invention include eukaryotic cells and viruses which have undergone insertion and/or deletion of one or more selected DNA sequences at specific genome sites. DNA sequences inserted into or deleted from engineered genome products of the invention may be whole genes or portions of genes such as gene promoter sequences, regulatory sequences, genes lacking coding sequences, and the like. Engineered eukaryotic cell and viral products of the invention preferably do not include the tk gene used in the manipulative procedures.

According to one aspect of the invention, upon the determination of a site for insertion or deletion of a selected DNA sequence in a eukaryotic cell or viral genome, a linear fragment of the genome is isolated which contains the site together with DNA sequences which normally precede and follow the site (i.e., the "left" and "right" flanking sequences). Genome fragment copies are made and are then manipulated to form: (a) a first altered fragment which includes a herpesvirus tk gene in a position intermediate the ends of the fragment; and (b) a second altered fragment which includes the selected DNA sequence insertion or deletion.

Preparation of the first and second altered fragments does not involve direct manipulation of the entire genome to be transformed but, rather, only specified portions thereof. The fragment manipulations may therefore be accomplished with readily available restriction endonuclease enzymes, preferably using DNA plasmids as support and amplification vehicles for the fragment.

When an intact, tk−, genome to be manipulated is contacted under suitable conditions with the first altered fragment, recombination occurs at the sites of DNA sequence homology between the genome and the fragments (i.e., at the right and left flanking sequences), resulting in the incorporation of the tk gene and associated flanking sequences into the genome. Recombinant genomes are selected through exposure to conditions strongly selective against propagation of a genome which is thymidine kinase deficient (tk−). Surviving genomes, which are tk+, are isolated and amplified.

Contacting a recombinant, tk+, genome as described above with the second altered fragment under suitable conditions allows recombination to again occur at the site of sequence homology, resulting in incorporation of a fragment having the desired insertion or deletion. Recombinant genomes are selected through exposure to conditions strongly selective against propagation of a genome which is tk+. Surviving, tk−, genomes thus include the desired DNA sequence insertion or deletion at the precise site desired, but need not include the herpesvirus tk marker gene.

If needed to facilitate selection procedures, the genome to be manipulated (e.g., a Herpes Zoster virus) may have endogenous tk gene function temporarily deleted or de-activated and later restored or reactivated.

Conditions selective against a tk− genome propagation preferably involve use of growth media including mixtures of hypoxanthine, aminopterin and thymidine ("HAT") which blocks the methylation of UMP to TMP as an alternative route to thymidine kinase catalyzed TMP synthesis. Conditions selective against a tk+ to genome propagation preferably involve use of nucleoside analogues such as thymine arabinoside ("AraT") which are phosphorylated by the viral thymidine kinase and poorly, or not at all, phosphorylated by the cellular enzyme.

DNA sequence insertions, deletions and substitutions at specific sites within a eukaryotic cell or viral genome according to the present invention allow manipulations and resultant products of considerable medical and commercial significance. In the area of pathogenic viruses, for example, practice of the invention permits introduction of minor specific sequence insertions and/or deletions which would not disrupt gene function completely but would nonetheless debilitate and hence attenuate the virus. Also made available through practice of the invention are vaccine viruses having a specific gene (e.g., one coding for an antigenic protein) deleted and replaced by a gene specifying an antigen to which a natural host organism is not normally exposed, thereby allowing for development of a distinct antibody profile in vaccinated animals. Vaccine viruses may also be modified to incorporate multiple copies of a selected gene (again, for example, one coding for a particular antigen) so that vaccinated animals receive an amplified antibody-generating stimulus.

Procedures of the invention can be employed to alter the normal promoter control of a selected gene either by insertion of the gene in a region under the control of a different promoter or insertion of a new or different promoter in a suitable region preceding the selected gene. Such altered genomes would allow, for example, transcription and expression of a gene in either a premature or delayed manner favorably altering the virus's antigenicity and pathogenicity characteristics without seriously altering in vitro growth characteristics. Manipulations of a type noted above for viruses are equally applicable to eukaryotic cell genomes.

Further aspects and advantages of the invention will be made apparent upon consideration of the following detailed description and accompanying drawings.

DESCRIPTION OF THE DRAWINGS

FIGS. 1 through 5 schematically illustrate practice of the process of the invention as employed in effecting deletion of a selected DNA sequence from a genome.

FIG. 1 illustrates a tk− genome containing the selected sequence to be deleted, together with its left and right flanking sequences.

FIGS. 2 and 3 illustrate steps involved in developing a first altered genome fragment.

FIG. 4 illustrates development of a second altered genome fragment.

FIG. 5 illustrates manipulations performed on the intact genome of FIG. 1 using the first and second altered genome fragments of FIGS. 3 and 4 to achieve deletion of the selected sequence.

FIGS. 6 through 9 schematically illustrate the constructions, recombinational events and phenotype verifications involved in effecting a deletion in the HSV-1 ICP No. 22 gene.

FIG. 6 illustrates construction of tk− plasmid pRB305 and tk−, ICP 22+ virus HSV-1 Δ305.

FIG. 7 illustrates construction of tk+, ICP 22-plasmid pRB321 and tk+, ICP 22- virus HSV-1 321.

FIG. 8 illustrates construction of ICP 22-plasmid pRB325 and tk−, ICP 22-virus HSV-1 Δ325.

FIG. 9 illustrates construction of the BamHI Q fragment of pRB103 (comprising the HSV tk sequence) and use of said fragment to convert the tk−, ICP 22-virus HSV-1 Δ325 of FIG. 8 into a tk+, ICP 22- HSV-1 virus having the desired deletion in the ICP No. 22 gene.

DETAILED DESCRIPTION

Figure 1:
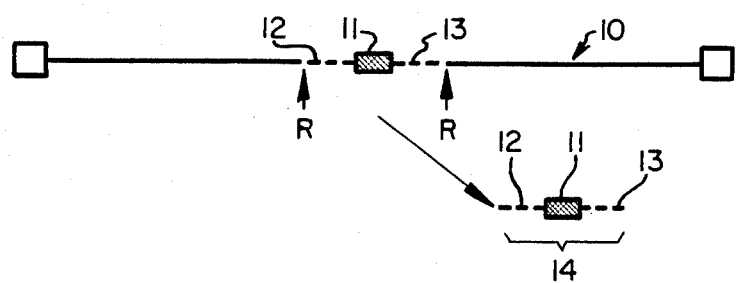
FIGS. 1–9 schematically illustrate the genetic manipulation procedures of the present invention. Throughout these Figures, sites of cleavage of DNA sequences with restriction endonucleases are represented by the symbol "R→".

The present invention provides methods for stably effecting the insertion or deletion of a selected DNA sequence at a specific site in a eukaryotic or viral genome to be manipulated comprising:

(1) isolating from said genome a linear DNA fragment comprising both (a) the specific site determined for insertion or deletion of selected DNA sequence and (b) flanking DNA sequences normally preceding and following said site;

(2) preparing first and second altered genome fragments from the fragment isolated in step (1),
   (a) said first altered fragment comprising the fragment including a herpesvirus thymidine kinase gene in a position intermediate the ends of said fragment, and
   (b) said second altered fragment comprising the fragment having said selected DNA sequence inserted therein or deleted therefrom;

(3) contacting said genome with said first altered fragment under conditions permitting recombination at sites of DNA sequence homology, selecting for a recombinant genome including said thymidine kinase gene, and isolating the recombinant genome; and (4) contacting the recombinant genome isolated in step (3) with said second altered fragment under conditions permitting recombination at sites of DNA sequence homology, selecting for a recombinant genome lacking said thymidine kinase gene, and isolating the recombinant genome product.

The present invention is clearly most advantageously practiced in effecting genetic manipulations in large, complex genomes as are present in eukaryotic cells and in viruses, such as herpesvirus, which infect higher orders or organisms. Manipulations involving smaller, less complex genomes found in bacterial phage viruses are nontheless within the scope of the invention. Exemplary eukaryotic cell genomes susceptible to manipulation include genomes of plant and animal cells. Exemplary pathogenic viral genomes susceptible to manipulation include herpesviruses (including human Herpes Simplex and Herpes Zoster), pseudorabies virus, bovine rhinotracheitis virus, equine abortion viruses, iridoviruses (African swine fever) and poxviruses.

Isolation of selected linear DNA fragments of genomes and of specific sequences to be inserted is accomplished through use of available restriction endonuclease enzymes with verification of fragment content made through electrophoresis and DNA hybridization with radioactive probes.

Amplification of isolated fragments is accomplished by straightforward gene amplification procedures such as are described in U.S. Pat. No. 4,237,224 and involve, e.g., circular bacterial plasmid DNA. Construction of plasmids is also described by the inventors and their co-workers in Post, et al., *P.N.A.S.*, 77, pp. 4201–4205 (1980).

Preparation of linear herpesvirus DNA fragments containing the thymidine kinase gene likewise proceeds by straightforward techniques. HSV-1 thymidine kinase gene, for example, is readily isolated as the Bam HI Q fragment of HSV-1.

Propagation of virus in practice of the invention may involve any number of suitable hosts. HSV-1 propagation, for example, may be on African green monkey (Vero) cells. Manipulations of viral genomes are preferably performed using a first cell line for transfection with DNA (e.g., rabbit skin cells) and a second line for selection of tk+ viruses (e.g., tk− human 143 cells). Cotransfections are carried out by modification of the calcium phosphate precipitation method described in the Mocarski, et al. publication, supra.

FIGS. 1 through 4 schematically illustrate practice of the process of the invention as employed in effecting deletion of a selected DNA sequence from a genome. In FIG. 1, reference numeral 10 designates a large genome containing the selected gene to be deleted 11 together with the left flanking sequence 12 and right flanking sequence 13. The genome is initially lacking any tk gene (or has had the tk gene deleted or deactivated) and hence has a tk− phenotype. Restriction endonuclease enzymes are employed to cleave genome 10 at the sites indicated to obtain a linear genome fragment 14 which comprises gene sequence 11 and flanking sequences 12 and 13.

Figure 2:
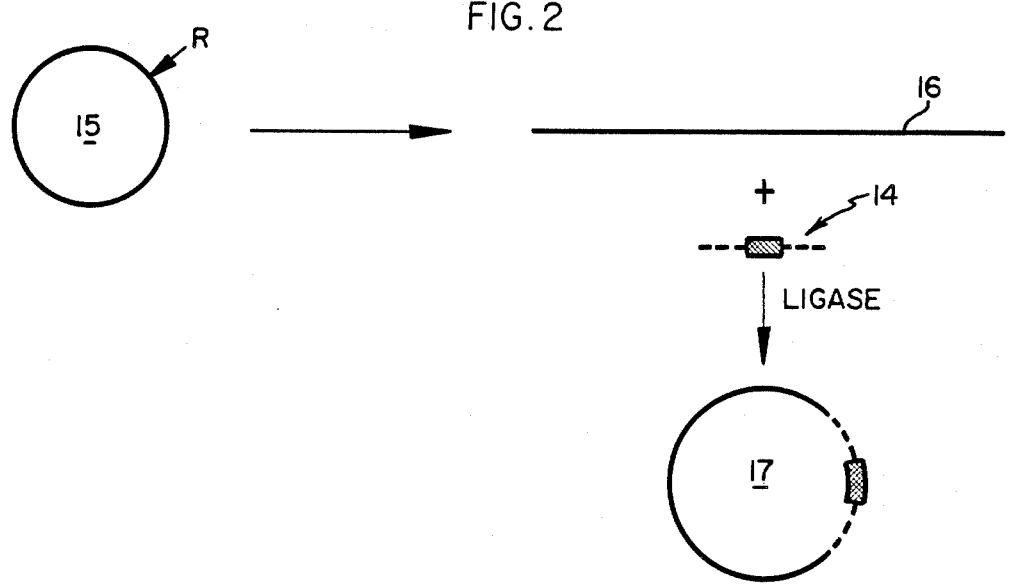

FIG. 2 illustrates the first stages of manipulations performed on genome fragment 14 to develop a first and second altered fragment. A suitable plasmid 15 is first cleaved with an endonuclease to form a linear strand 16 which is incubated with fragment 14 and a suitable ligase enzyme to form hybrid plasmid 17. The plasmid is amplified in a suitable host to develop numerous copies.

Figure 3:
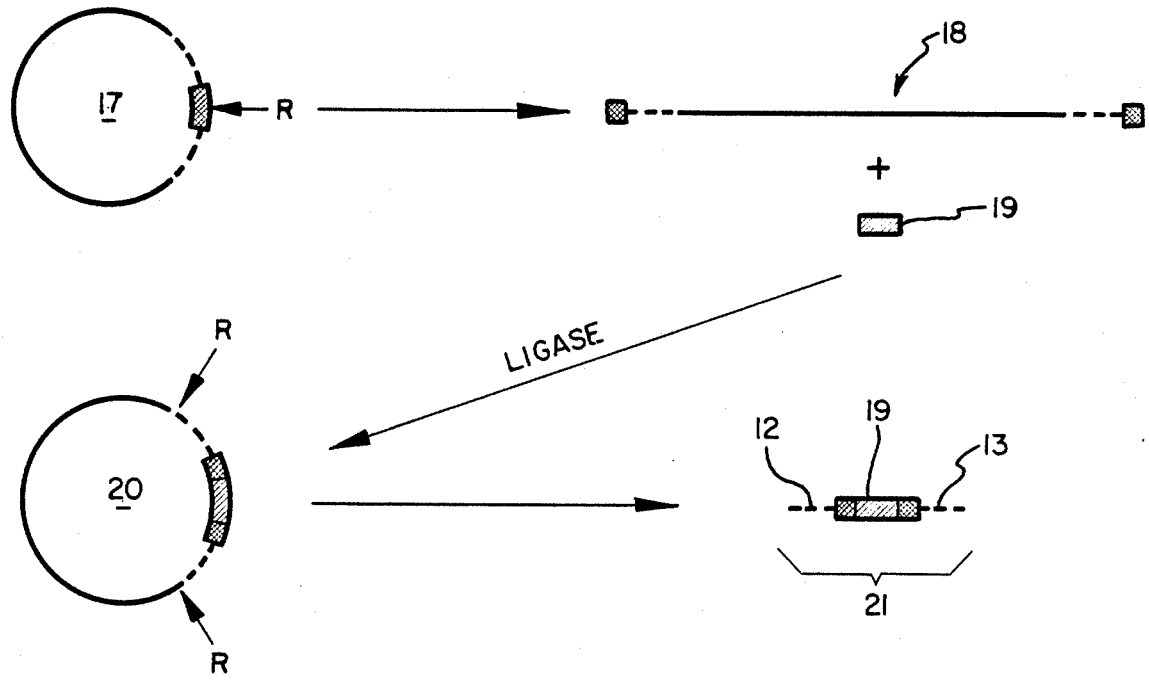

FIG. 3 illustrates a manipulation of plasmid 17 to form a first altered fragment. Cleavage of plasmid 17 develops linear fragment 18 which is incubated with a herpesvirus thymidine kinase gene 19 in the presence of a ligase enzyme to form hybrid plasmid 20. The hybrid is amplified in a suitable host to develop numerous copies and then cleaved to provide copies of first altered genome fragment 21. It should be noted that while the figure illustrates insertion of the thymidine kinase gene at a position within gene sequence 11, insertion at any site intermediate ends of flanking sequences 12 and 13 (i.e., a site preserving the integrity of both right and left flanking sequences) is appropriate.

Figure 4:
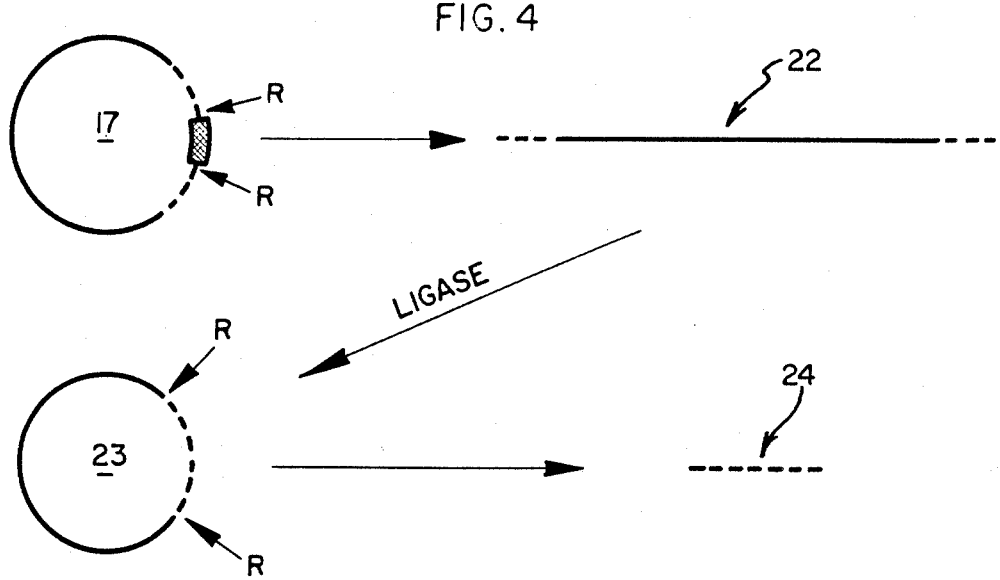

FIG. 4 illustrates manipulation of plasmid 17 to form a second altered fragment. Cleavage of plasmid at sites within the flanking sequences 12 and 13 and immediately adjacent gene 11 to form linear fragment 22 which is reassembled in circular form 23 by suitable ligase enzyme treatment. The plasmid is amplified in a suitable host to develop numerous copies and then cleaved to provide copies of second altered gene fragment 24.

Figure 5:
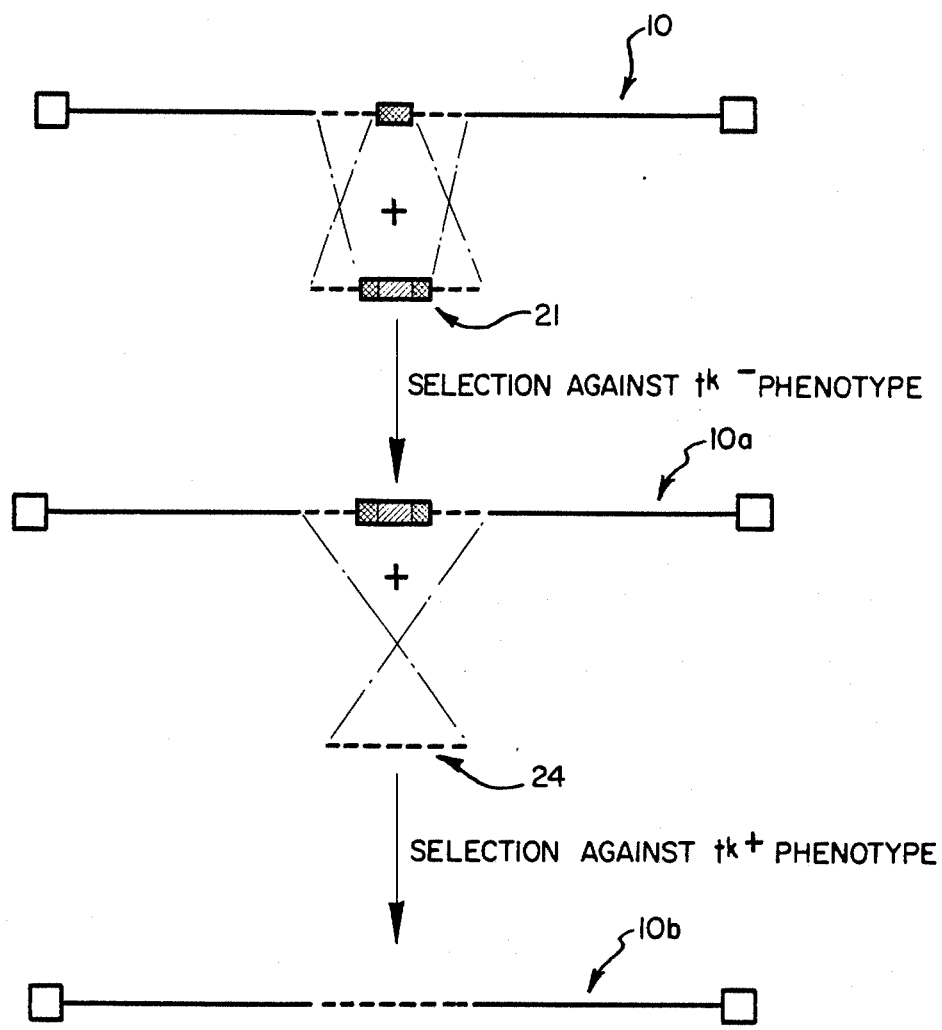
Figure 6:
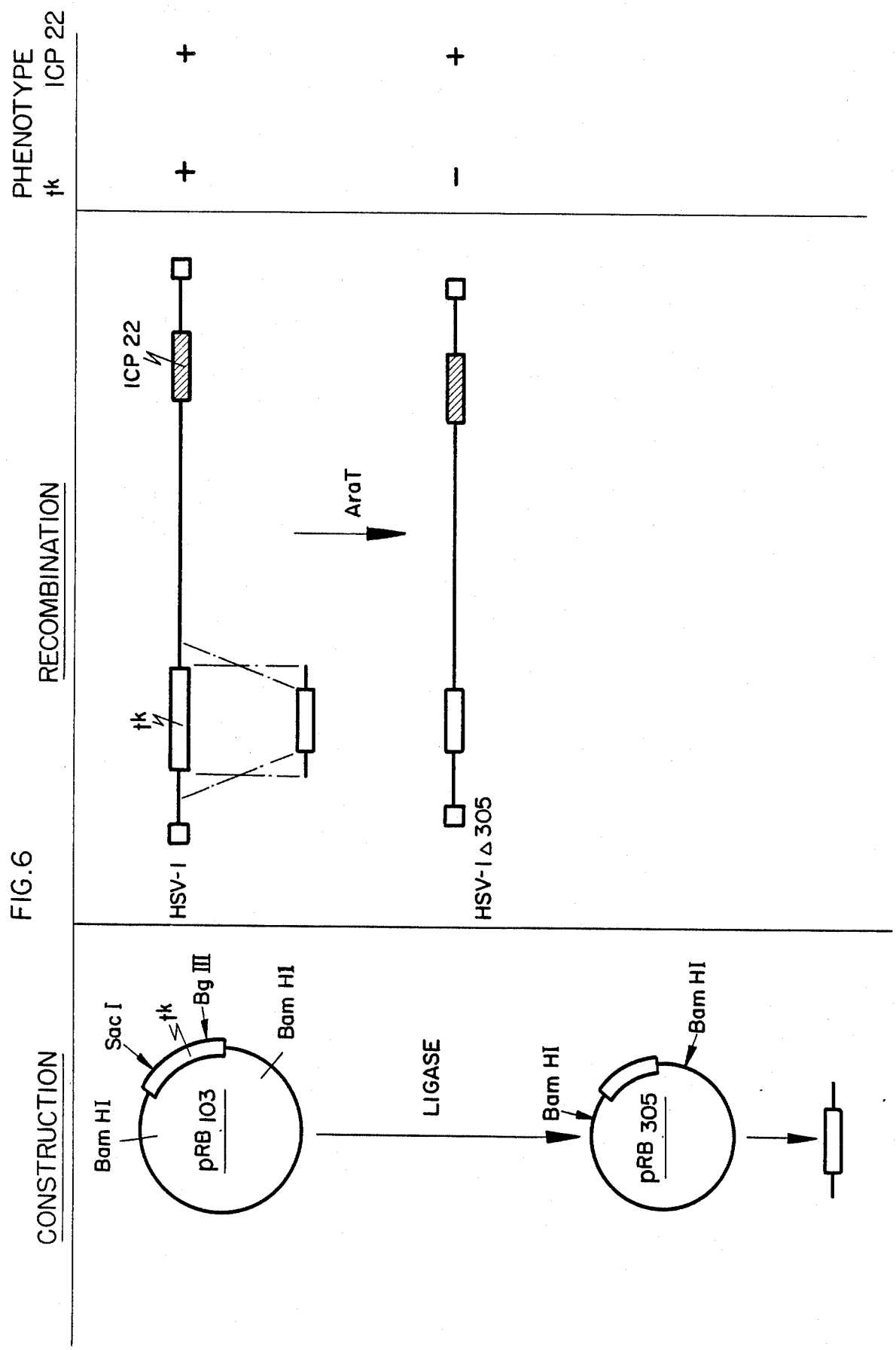
Figure 7:
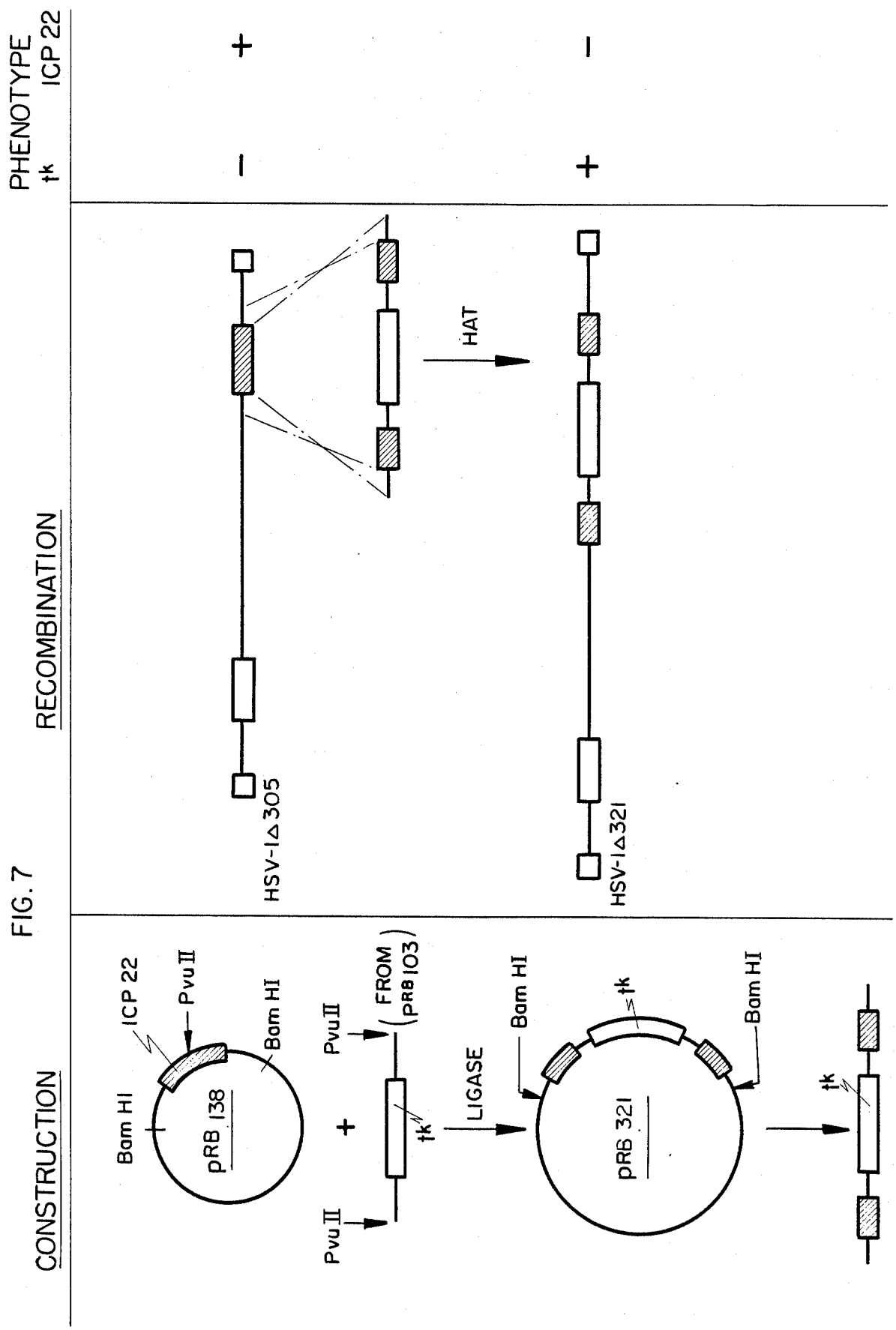
Figure 8:
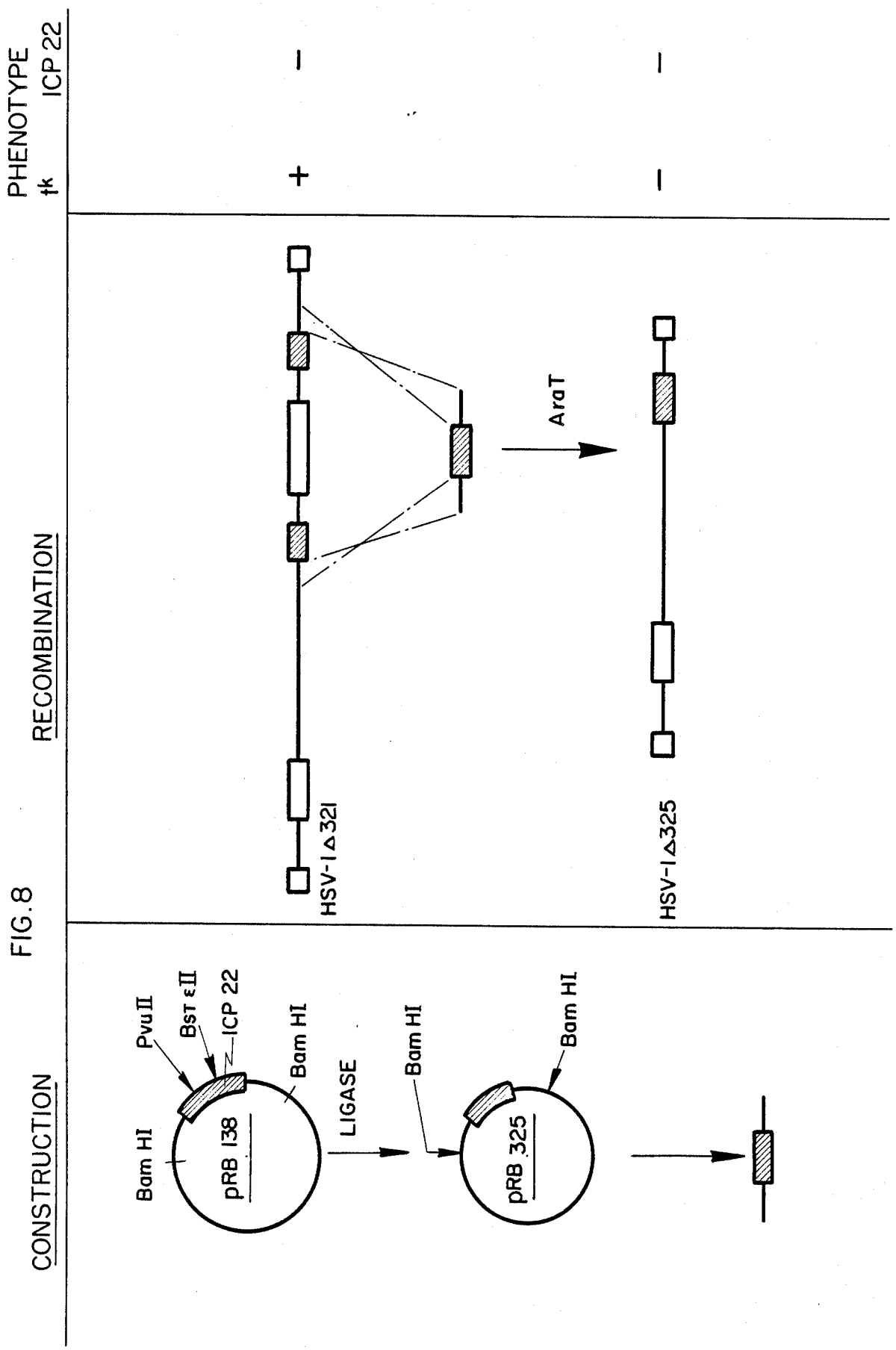

FIG. 5 illustrates the manipulations performed on the intact genome using first and second altered genome fragments. The first altered fragment 21 is contacted with intact genome 10 under conditions favoring recombination (as indicated by the hatched lines), resulting in the formation of recombinant genome 10a which includes the thymidine kinase gene. Recombinant genomes are isolated through selection against the tk⁻ phenotype. Copies of recombinant genome 10a are are then incubated with copies of the second altered fragment 24 under conditions favoring recombination, resulting in formation of recombinant genome 10b which is lacking both the thymidine kinase gene and the DNA sequence to be deleted but which otherwise includes all materials present in the original intact genome.

It will be readily apparent from the above outline of procedures concerning deletion of a DNA sequence that essentially the same processes are applicable in manipulations involving insertion of a selected DNA sequence at a predetermined site along a large genome. The genome fragment would include the predetermined site together with the DNA sequences which precede and follow the site. The first altered fragment would include the herpesvirus tk gene inserted intermediate the ends of the fragment and the second altered fragment would include the DNA sequence (i.e., a selected gene or gene fragment) at the site and between the left and right flanking sequences. A selected gene or gene fragment so inserted may be a copy of a DNA sequence already present in the genome or may be a wholly exogenous sequence.

It is equally apparent that among the manipulations which may be performed according to the above procedures are "substitution" of selected DNA sequences. In such a case, the genome fragment would include a DNA sequence to be "replaced" and preparation of the second altered fragment would include both the steps of deleting a selected sequence and inserting in its place a different DNA sequence.

It will also be seen that the above procedures of deletion and insertion may be performed sequentially to effectively delete a gene or gene fragment from one locus of a genome and insert the same in one or more different loci of the genome wherein, for example, the sequence will be under the control of a different promoter and may be expressed earlier or later.

Finally, the above procedures are readily applicable to the simple insertion or deletion or inactivation of a herpesvirus thymidine kinase gene itself. If the tk gene is to be inserted in a tk⁻ genome, one need only isolate a genome fragment including the proposed insertion site and flanking sequences, prepare a first altered fragment as specified, and effect recombination of the first altered fragment with the intact genome—selecting for recombinant genomes including the tk gene. If the tk gene is to be deleted from a tk⁺ genome, the isolated genome fragment will contain the tk gene and flanking sequences. Only an altered fragment of the "second" type (i.e., one involving a tk gene DNA sequence deletion) need be prepared. Such a tk gene-free altered fragment is recombined with the intact genome and selection for recombinant genomes which are tk⁻ is carried out. If inactivation of a tk gene in a genome to be otherwise manipulated is desired, the procedures noted immediately above are employed to effect either an insertion of a transcription- or expression-disrupting DNA sequence or deletion of a tk gene portion which is essential to transcription or expression.

The following example illustrates practice of the present invention to develop a specific manipulated viral genome product, i.e., a human Herpes Simplex HSV-1 virus which includes the entire wild-type genome except for the specific deletion of a gene specifying the infected cell polypeptide (ICP) No. 22.

EXAMPLE 1

1. Background Information Concerning the Manipulated Genome

Human Herpes Simplex (HSV-1) virus contains a DNA genome with a molecular weight of approximately 100 million. Approximately 50 infected cell polypeptides (ICP's) have been identified as virus-specific and these form at least three groups, designated as $\alpha$, $\beta$ and $\gamma$, whose synthesis is coordinately regulated and sequentially ordered in a cascade fashion. [See, e.g., Honess & Roizman, *J. Virol.*, 14, pp. 8–19 (1974) and *P.N.A.S.*, 72, pp. 1276–1295 (1975)]. The $\alpha$ genes are responsible for polypeptide synthesis which reaches maximal rates from 2 to 4 hours after infection. To date, five $\alpha$ genes (coding for ICP Nos. 4, 0, 22, 27 and 47) have been identified. Functional $\alpha$ polypeptides are required for transcription of $\beta$ genes. The $\beta$ gene polypeptides, which include viral DNA polymerase and thymidine kinase, are made at maximal rates between 5 and 7 hours after infection. One or more $\beta$ polypeptides are necessary for termination of synthesis of $\alpha$ polypeptides and initiation of transcription of $\gamma$ genes. The $\gamma$ polypeptides, which include those involved in the virion structure, are synthesized at maximal rates between 12 and 17 hours after infection.

The $\alpha$ genes of HSV-1 have been mapped [See, e.g., Morse, et al., *J. Virol.*, 26, pp. 389–410 (1978); Anderson, et al., *J. Virol.*, 34, pp. 9–27 (1980); Preston, et al., *J. Virol.*, 28, pp. 499–517 (1978); Clements, et al., *Nucleic Acids Res.*, 7, pp. 77–91 (1979) and Mackem, et al., *P.N.A.S.*, 77, pp. 7122–7126 (1980)] but information regarding the function of the genes is rather meager. While ICP No. 0 appears to be unstable, ICP Nos. 4, 22 and 27 have been shown to be stable phosphoproteins. Although phosphate appears to cycle on and off ICP Nos. 4, 22 and 27 and it has been suggested that these proteins function throughout the HSV-1 reproductive cycle, conditional lethal mutations have only been obtained in the α ICP No. 4 gene, indicating that the other ICP's may be more involved in the establishment of latency rather than viral replication.

Figure 9:
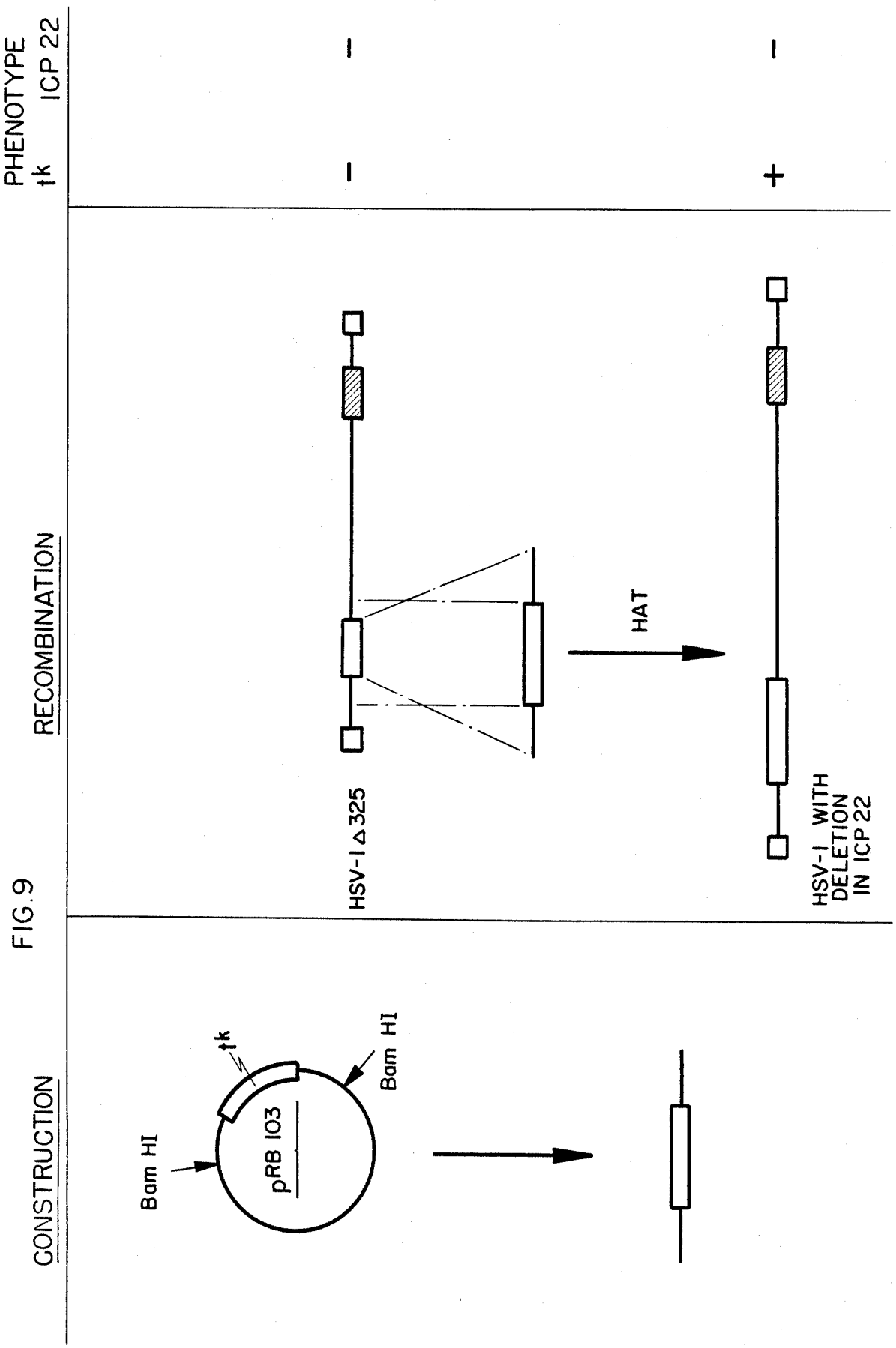

The deletion study of the present example was performed to determine, first, whether the α gene directed ICP 22 protein was essential for viral replication of HSV-1 and, if not, whether a specific partial deletion of the gene which left the N terminal intact (and the consequent transcription of the truncated gene and formation of a truncated ICP 22 protein) would affect antigenicity, pathogenicity and/or the capacity of HSV-1 to enter a latency stage.

2. Manipulative Procedures

The procedures involved in effecting a deletion in the HSV-1 ICP No. 22 gene will be better understood through reference to FIGS. 6 through 9 which schematically illustrate the constructions, recombinational events and phenotype verifications performed on genomes involved in the recombinational events.

Because the HSV-1 genome to be manipulated contains an endogenous tk gene within its genome and because the procedures of the invention involve selection for the presence of the endogenous tk gene, it was first necessary to manipulate the genome to delete at least a portion of the tk gene. This first involved the construction (FIG. 6) of a plasmid, pRB305, containing the tk gene together right and left flanking sequences but with a large number of base pairs deleted. Briefly stated, the plasmid pRBl03 (a pBR322 derivative containing the HSV-1 Bam HI Q fragment) was digested with both Sac I and Bgl II. Inasmuch as pBR322 lacks Sac I or Bgl II cleavage sites, these enzymes cleaved only within the Bam HI Q fragment and removed a 500 base pair fragment coding for the N-terminal amino acids of the thymidine kinase. The large linear fragment was then circularized by ligation. However, because Sac I ends have protruding 3′ nucleotides and Bgl II ends have protruding 5′ nucleotides, the protruding sequences were digested with S11 nuclease before ligation of the linear DNA. The S1 reaction was allowed to proceed to the extent that the digestion extended beyond the single-stranded termini. As a consequence, the new plasmids obtained by transformation of E. coli with the ligated DNA contained deletions ranging from 500 to nearly 700 base pairs. The plasmid pRB305, selected for subsequent work contained a deletion of nearly 700 base pairs beginning from the right of the Bgl II cleavage site and extending leftward beyond the Sac I cleavage site.

As indicated by the recombination illustrated in FIG. 6, the Bam HI fragment contained in pRB305 was co-transfected with HSV-1 into a continuous line of rabbit skin cells according to a variation of the calcium phosphate precipitation method described in Mocarski, et al., supra. Viral genomes resulting from transfection (all initially displaying the tk+ and ICP22+ phenotype) were selected for the tk−, ICP22+ phenotype evidencing recombination of the "deleted" tk gene fragment into the viral genome by plating viral progeny of transfected cells in Vero (African green monkey) cells overlapped with medium containing thymmidine arabinoside (Ara T, Raglo Chemical Co., Edmonton, Alberta). The selected, surviving, tk− virus was designated HSV-1 Δ305.

The next construction involved in the procedure (FIG. 7) was the insertion of the HSV-1 tk gene into the structural sequence of the ICP No. 22 gene. A 2 kilobase fragment of HSV-1 formed by Pvu II cleavage contains an entire functional HSV-1 tk gene. The ICP No. 22 gene is known to be located within the Bam HI N fragment of HSV-1 and its coding sequences span the portion of the fragment which includes a Pvu II cleavage site. This site is the only Pvu II cleavage site in Bam HI N and thus it is the only Pvu II cleavage site in pRBl38, a plasmid consisting of the Bam HI N fragment inserted in a vector plasmid pRB3 (pBR322 with the Pvu II site deleted).

Plasmid pRB32l was thus prepared by insertion of an HSV-1 Pvu II fragment containing the tk gėne into the Pvu II site in pRBl38, thereby interrupting the coding sequences of the ICP No. 22 gene.

The Bam HI digest of pRB32l plasmid DNA was cotransfected into rabbit skin cells with intact HSV-1 Δ305 isolated from the preceeding recombination procedure. The progeny of transfection were then used to infect tk− human 143 cells in HAT medium, providing conditions under which only tk+ viruses can grow. Thus the viral genomes resulting from transfection (all initially displaying the $tk^{31}$ and ICP22+ phenotype) were selected for the tk+, ICP22− phenotype evidencing recombination (illustrated in FIG. 7) of the tk− inserted ICP No. 22 gene into the genome. The selected, surviving, tk+ virus was designated HSV-1 Δ321.

It is noteworthy that under the above.-noted conditions two types of tk+ recombinant viruses were obtained. The Pvu II fragment containing the thymidine kinase gene in pRB321 spans the deleted sequences in HSV-1 Δ305, allowing a recombination event that restores a functional thymidine kinase gene by replacing the deleted sequence in HSV-1 Δ305. Such recombinants, which are really wild type HSV-1 (F+), represented about 90% of the selected viruses. These may be segregated from the desired HSV-1 Δ321 virus by restriction endonuclease patterns of their DNA's.

The third construction involved in the procedure (FIG. 8) was effecting a specific, inactivating, deletion in the ICP No. 22 gene. Plasmid pRB325 was produced by digesting pRBl38 with Pvu II and BstE II (both of which cleave pRBl38 only once, within the Bam HI N fragment previously noted to contain the entire HSV-1 ICP No. 22 gene), and then treating with S1 nuclease and DNA ligase. The size of the deletion in pRB325 was determined to be about 0.7 kilobases.

The Bam HI digest of the pRB325 deletion plasmid was co-transfected in rabbit skin cells with intact HSV-1 Δ321 isolated from the preceding recombination procedure. The progeny of transfection were then used to infect Vero cells in Ara T medium, providing conditions under which only $tk^{31}$ viruses can grow. Thus, the resulting viral genomes (all initially displaying the tk+ and ICP22− phenotype) were selected for the $tk^{31}$, ICP22− phenotype evidencing recombination (illustrated in of FIG. 8) of the "deleted" ICP 22 gene into the genome. The selected, surviving, $tk^{31}$ virus was designated HSV-1 Δ325.

The final construction involved in the procedure (in FIG. 9) was the simple preparation of a Bam HI Q fragment from pRB103. The prepared fragment was co-transfected into rabbit skin cells with intact HSV-1 Δ325 virus. The progeny of transfection were used to infect $tk^{31}$ human 143 cells in HAT medium, providing conditions under which only tk+ viruses can grow. Viral genomes resulting from transfection (all initially displaying the tk−, ICP22− phenotype) were selected for the tk+, ICP22− phenotype evidencing recombination (illustrated FIG. 9) of the intact tk gene into the genome.

Successful propagation of the HSV-1 virus having a deletion in the ICP No. 22 gene demonstrated that the ICP 22 protein was not essential for replication. Preliminary screening tests have indicated that the virus has reduced pathogenicity in mice.

While the above illustrative example involves use of a tk gene derived from human Herpes Simplex 1 (HSV-1) virus, it will be understood that tk genes originating in other herpesviruses (such as human Herpes Virus 2 and Herpes Zoster) are equally useful. Similarly, while an E. coli/pBR322 host/vector system is employed in the steps of forming and amplifying altered genome fragments for use in the above example, many other host/vector combinations are suitable.

Numerous modifications and variations of the invention are expected to occur to those of ordinary skill in the art upon consideration of the foregoing description thereof. Therefore, only such limitations as appear in the appended claims should be placed thereon.

What is claimed is:

1. A method for stably effecting the insertion or deletion of a selected DNA sequence at a specific site in a viral genome, said method comprising:
    (1) isolating from said genome a linear DNA fragment comprising both (a) the specific site determined for insertion or deletion of selected DNA sequence and (b) flanking DNA sequences normally preceding and following said site;
    (2) preparing first and second altered genome fragments from the fragment isolated in step (1).
    (a) said first altered fragment comprising the fragment comprising a thymidine kinase gene in a position intermediate the ends of said fragment, and
    (b) said second altered fragment comprising the fragment having said selected DNA sequence inserted therein or deleted therefrom;
    (3) contacting said genome with said first altered fragment under conditions permitting recombination at sites of DNA sequence homology, selecting for a recombinant genome comprising said thymidine kinase gene, and isolating the recombinant genome; and
    (4) contacting the recombinant genome isolated in step (3) with said second altered fragment under conditions permitting recombination at sites of DNA sequence homology, selecting for a recombinant genome lacking said thymidine kinase gene, and isolating the recombinant genome product.

2. The method according to claim 1 wherein the genome is a pathogenic viral genome.

3. The method according to claim 1 wherein said thymidine kinase gene is of human Herpes Virus 1 origin.

4. The method according to claim 1 wherein the step of selecting for a recombinant genome comprising said thymidine kinase gene comprises the step of exposing the recombinant genome to a growth medium comprising HAT.

5. The method according to claims 1 or 4 wherein the step of selecting for a recombinant genome not comprising said thymidine kinase gene comprises the step of exposing the recombinant genome to a growth medium comprising AraT.

6. The method according to claim 1 wherein the method comprises the step of deleting one selected DNA sequence and wherein the method comprises the step of inserting another selected DNA sequence.

7. The method according to claim 6 wherein said deleting and inserting steps are effected at substantially the same site in the genome.

8. The method according to claim 6 wherein said deleting and inserting steps are effected at different sites in the genome.

9. The method according to claim 8 wherein the DNA sequences inserted and deleted are identical.

* * * * *